US00PP27711P3

(12) United States Plant Patent
Vitten et al.

(10) Patent No.: US PP27,711 P3
(45) Date of Patent: Feb. 28, 2017

(54) STRAWBERRY PLANT NAMED 'DRISSTRAWFORTYSIX'

(50) Latin Name: *Fragaria×ananassa*
Varietal Denomination: DrisStrawFortySix

(71) Applicant: Driscoll's, Inc., Watsonville, CA (US)

(72) Inventors: Matthias D. Vitten, Aptos, CA (US); Carlos D. Fear, Aptos, CA (US); Katalin Pakozdi, Maidstone (GB)

(73) Assignee: Driscoll's, Inc., Watsonville, CA (US)

( * ) Notice: Subject to any disclaimer, the term of this patent is extended or adjusted under 35 U.S.C. 154(b) by 0 days.

(21) Appl. No.: 14/545,234

(22) Filed: Apr. 10, 2015

(65) Prior Publication Data

US 2016/0302339 P1 Oct. 13, 2016

(51) Int. Cl.
*A01H 5/08* (2006.01)

(52) U.S. Cl.
USPC ..... Plt./208

(58) Field of Classification Search
USPC ..... Plt./208
See application file for complete search history.

(56) References Cited

U.S. PATENT DOCUMENTS

| | | | |
|---|---|---|---|
| PP1,745 | P | 8/1958 | Lang |
| PP3,981 | P | 11/1976 | Bringhurst et al. |
| PP4,487 | P | 11/1979 | Bringhurst et al. |
| PP4,538 | P | 5/1980 | Bringhurst et al. |
| PP5,262 | P | 7/1984 | Voth et al. |
| PP5,265 | P | 7/1984 | Voth et al. |
| PP5,266 | P | 7/1984 | Bringhurst et al. |
| PP5,300 | P | 10/1984 | Johnson, Jr. |
| PP5,480 | P | 5/1985 | Nakagawa |
| PP5,840 | P | 12/1986 | Johnson, Jr. et al. |
| PP6,191 | P | 5/1988 | Johnson, Jr. et al. |
| PP6,231 | P | 7/1988 | Johnson, Jr. et al. |
| PP6,578 | P | 1/1989 | Voth et al. |
| PP6,579 | P | 1/1989 | Bringhurst et al. |
| PP7,024 | P | 9/1989 | Johnson, Jr. et al. |
| PP7,172 | P | 2/1990 | Voth et al. |
| PP7,522 | P | 5/1991 | Johnson, Jr. et al. |
| PP7,614 | P | 8/1991 | Bringhurst et al. |
| PP7,615 | P | 8/1991 | Bringhurst et al. |
| PP8,086 | P | 1/1993 | Nelson et al. |
| PP8,205 | P | 4/1993 | Nelson et al. |
| PP8,649 | P | 3/1994 | Sjulin et al. |
| PP8,661 | P | 3/1994 | Bringhurst et al. |
| PP8,708 | P | 5/1994 | Voth et al. |
| PP8,745 | P | 5/1994 | Sjulin et al. |
| PP9,130 | P | 5/1995 | Sjulin et al. |
| PP9,909 | P | 6/1997 | Ackerman et al. |
| PP10,221 | P | 2/1998 | Sjulin et al. |
| PP10,534 | P | 8/1998 | Sjulin et al. |
| PP10,642 | P | 10/1998 | Amorao et al. |
| PP11,035 | P | 8/1999 | Mowrey et al. |
| PP11,277 | P | 3/2000 | Gilford et al. |
| PP11,279 | P | 3/2000 | Gilford et al. |
| PP11,522 | P | 9/2000 | Amorao et al. |
| PP11,548 | P | 10/2000 | Amorao et al. |
| PP11,554 | P | 10/2000 | Sjulin et al. |
| PP11,639 | P | 11/2000 | Mowrey et al. |
| PP12,186 | P2 | 11/2001 | Gilford et al. |
| PP12,436 | P2 | 3/2002 | Amorao et al. |
| PP12,577 | P2 | 4/2002 | Amorao et al. |
| PP12,817 | P2 | 7/2002 | Gilford et al. |
| PP12,889 | P2 | 8/2002 | Lamb et al. |
| PP12,899 | P2 | 9/2002 | Mowrey et al. |
| PP13,386 | P2 | 12/2002 | Mowrey et al. |
| PP13,469 | P3 | 1/2003 | Larson et al. |
| PP14,005 | P3 | 7/2003 | Amorao et al. |
| PP14,062 | P3 | 8/2003 | Amorao et al. |
| PP14,109 | P3 | 8/2003 | Gilford et al. |
| PP14,771 | P3 | 5/2004 | Amorao et al. |
| PP15,145 | P2 | 9/2004 | Mowrey et al. |
| PP15,308 | P2 | 11/2004 | Sjulin et al. |
| PP15,375 | P2 | 11/2004 | Mowrey et al. |
| PP15,435 | P2 | 12/2004 | Sjulin et al. |
| PP15,596 | P2 | 3/2005 | Amorao et al. |
| PP15,731 | P2 | 4/2005 | Amorao et al. |
| PP15,752 | P2 | 5/2005 | Gilford et al. |
| PP16,070 | P2 | 10/2005 | Gilford et al. |
| PP16,238 | P2 | 2/2006 | Amorao et al. |
| PP16,241 | P2 | 2/2006 | Mowrey et al. |
| PP16,298 | P2 | 2/2006 | Gilford et al. |
| PP16,299 | P2 | 2/2006 | Gilford et al. |
| PP16,475 | P2 | 4/2006 | Gilford et al. |
| PP16,558 | P3 | 5/2006 | Lopez |
| PP18,000 | P2 | 9/2007 | Meulenbroek |
| PP18,040 | P3 | 9/2007 | Mowrey et al. |
| PP18,041 | P3 | 9/2007 | Gilford |
| PP18,458 | P2 | 1/2008 | Ferguson et al. |
| PP18,575 | P3 | 3/2008 | Amorao et al. |
| PP18,878 | P2 | 6/2008 | Mowrey et al. |
| PP19,240 | P2 | 9/2008 | Gilford et al. |
| PP19,673 | P3 | 2/2009 | Ferguson et al. |
| PP19,767 | P2 | 2/2009 | Shaw et al. |
| PP20,248 | P3 | 9/2009 | Rogers et al. |
| PP20,701 | P2 | 2/2010 | Gilford et al. |
| PP20,731 | P2 | 2/2010 | Mowrey et al. |
| PP20,733 | P2 | 2/2010 | Mowrey et al. |
| PP20,735 | P2 | 2/2010 | Ferguson |
| PP20,775 | P2 | 2/2010 | Mowrey et al. |
| PP20,922 | P2 | 4/2010 | Gilford et al. |
| PP21,538 | P2 | 11/2010 | Gilford et al. |
| PP21,559 | P2 | 12/2010 | Ferguson et al. |
| PP21,762 | P2 | 3/2011 | Stewart et al. |
| PP22,040 | P3 | 7/2011 | Stewart et al. |
| PP22,218 | P2 | 11/2011 | Ferguson |
| PP22,247 | P2 | 11/2011 | Ferguson |
| PP23,107 | P2 | 10/2012 | Ferguson et al. |

(Continued)

OTHER PUBLICATIONS

Kibbe et al, U.S. Appl. No. 14/545,991, filed Jul. 15, 2015, titled "Strawberry Plant Named Drisstrawfortynine".

(Continued)

*Primary Examiner* — Anne Grunberg
(74) *Attorney, Agent, or Firm* — Morrison & Foerster LLP

(57) ABSTRACT

A new and distinct variety of strawberry plant named 'DrisStrawFortySix' particularly characterized by medium red, sweet fruit, a globose—semi-upright plant habit, and early harvest maturity, is disclosed.

2 Drawing Sheets

(56) References Cited

U.S. PATENT DOCUMENTS

| | | | |
|---|---|---|---|
| PP23,148 | P2 | 10/2012 | Gilford et al. |
| PP23,377 | P2 | 2/2013 | Ferguson et al. |
| PP23,378 | P2 | 2/2013 | Pullen et al. |
| PP23,382 | P2 | 2/2013 | Ferguson et al. |
| PP23,383 | P2 | 2/2013 | Ferguson et al. |
| PP23,400 | P2 | 2/2013 | Ferguson et al. |
| PP23,401 | P2 | 2/2013 | Pullen et al. |
| PP23,459 | P2 | 3/2013 | Stewart et al. |
| PP23,506 | P3 | 4/2013 | Ferguson et al. |
| PP23,517 | P3 | 4/2013 | Ferguson et al. |
| PP24,096 | P3 | 12/2013 | Fear et al. |
| PP24,317 | P3 | 3/2014 | Ferguson et al. |
| PP24,333 | P3 | 3/2014 | Vitten et al. |
| PP24,395 | P3 | 4/2014 | Vitten et al. |
| PP24,533 | P3 | 6/2014 | Ferguson et al. |
| PP24,745 | P2 | 8/2014 | Vitten et al. |
| PP25,408 | P3 | 4/2015 | Vitten et al. |
| PP25,437 | P3 | 4/2015 | Vitten et al. |
| PP25,698 | P3 | 7/2015 | Ferguson et al. |
| PP25,699 | P3 | 7/2015 | Stewart et al. |
| PP25,747 | P3 | 7/2015 | Kibbe et al. |
| PP25,866 | P3 | 9/2015 | Ferguson et al. |
| PP26,800 | P3 | 6/2016 | Stewart et al. |
| PP26,801 | P3 | 6/2016 | Stewart et al. |
| PP26,802 | P3 | 6/2016 | Rodriguez Alcazar et al. |
| 2003/0079263 | P1 | 4/2003 | Gilford et al. |
| 2013/0276182 | P1 | 10/2013 | Fear et al. |
| 2016/0270276 | P1 | 9/2016 | Vitten et al. |

OTHER PUBLICATIONS

Ferguson et al, U.S. Appl. No. 14/545,992, filed Jul. 15, 2015. titled "Strawberry Plant Named Drisstrawfortyseven".

Kibbe et al, U.S. Appl. No. 14/756,125, filed Aug. 4, 2015, titled "Strawberry Plant Named Drisstrawfortyeight".

Vitten et al, U.S. Appl. No. 14/999,062, filed Mar. 25, 2016 titled "Strawberry Plant Named Drisstrawfifty".

Genus and species: *Fragaria×ananassa.*

Variety denomination: 'DrisStrawFortySix'.

BACKGROUND OF THE NEW PLANT

The present invention relates to a new and distinct strawberry variety designated 'DrisStrawFortySix' and botanically known as *Fragaria×ananassa*. This new strawberry variety was discovered in Kent, United Kingdom in June 2010 and originated from a cross between the proprietary female parent 'DrisStrawThirtyTwo' (U.S. Plant Pat. No. 24,333) and the proprietary male parent 'KGEM 0631-001' (unpatented). A single plant was selected and asexually propagated via tissue culture and vegetative cuttings in Kent, United Kingdom in 2010.

'DrisStrawFortySix' underwent further testing in Kent, United Kingdom from 2010-2014. The present invention has been found to retain its distinctive characteristics through successive asexual propagations via stolons and tissue culture.

SUMMARY OF THE INVENTION

The following are the most outstanding and distinguishing characteristics of this new cultivar when grown under normal horticultural practices in Kent, United Kingdom.

1. Medium red, sweet fruit;
2. Globose—semi-upright plant habit; and
3. Early harvest maturity.

DESCRIPTION OF THE PHOTOGRAPHS

The accompanying color photographs show typical specimens of the new variety at various stages of development. The colors shown are as true as can be reasonably obtained by conventional photographic procedures. The photographs were taken from ten to twelve-month-old plants.

DESCRIPTION OF THE NEW VARIETY

Figure 1:
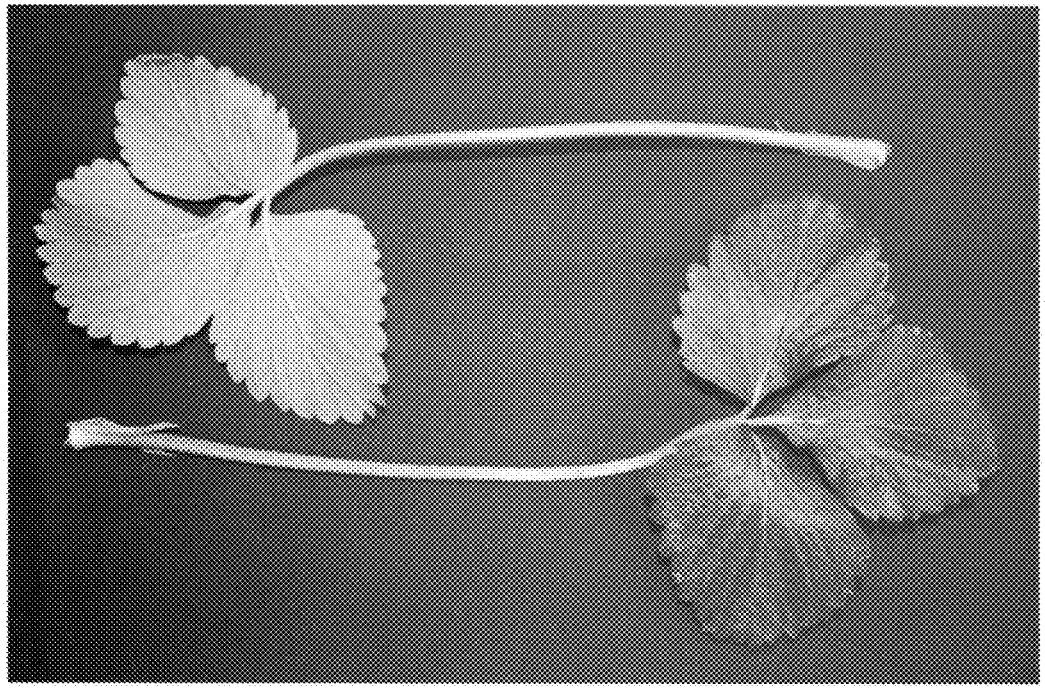
FIG. 1 shows upper and lower surfaces of the leaves of the plant with three leaflets.
Figure 2:
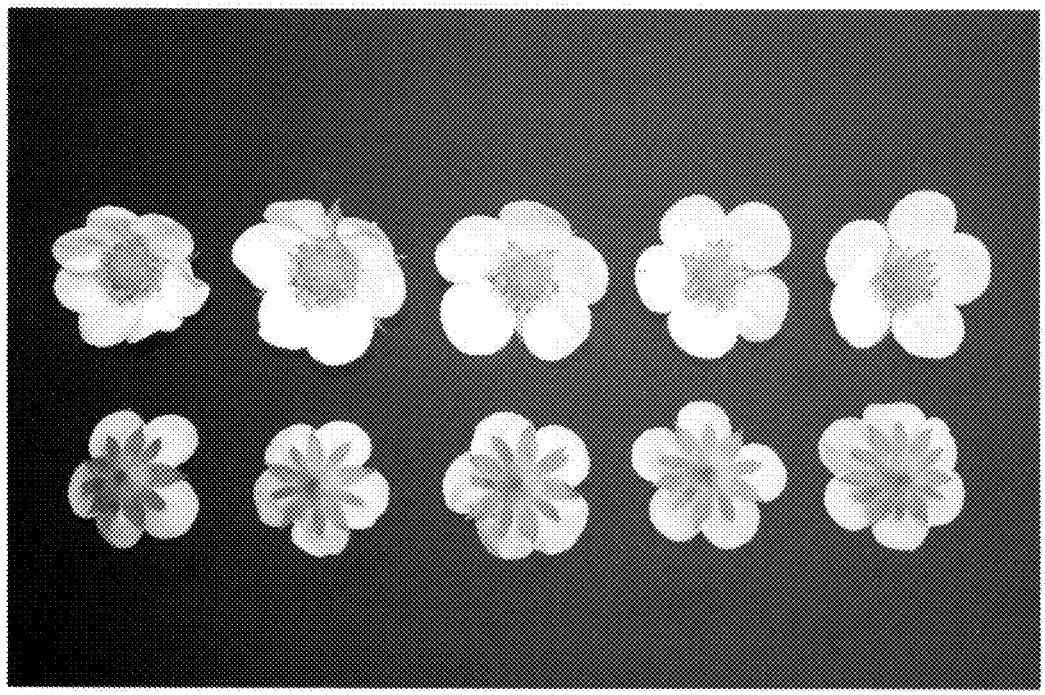
FIG. 2 shows both upper and lower surfaces of the flowers.
Figure 3:
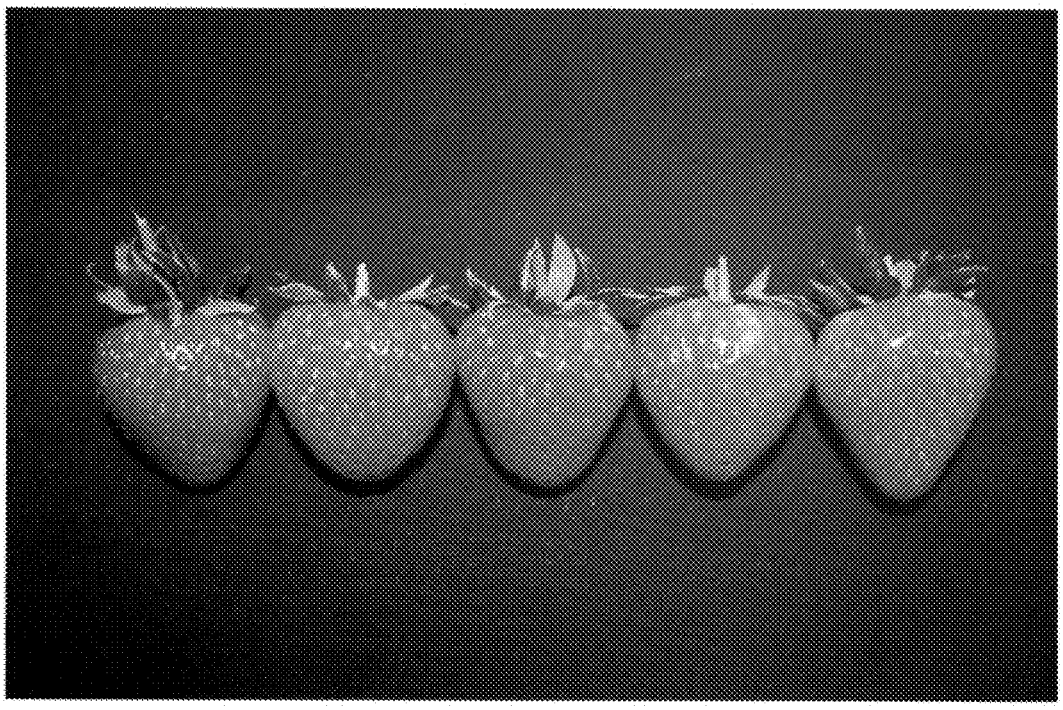
FIG. 3 shows the whole fruit.
Figure 4:
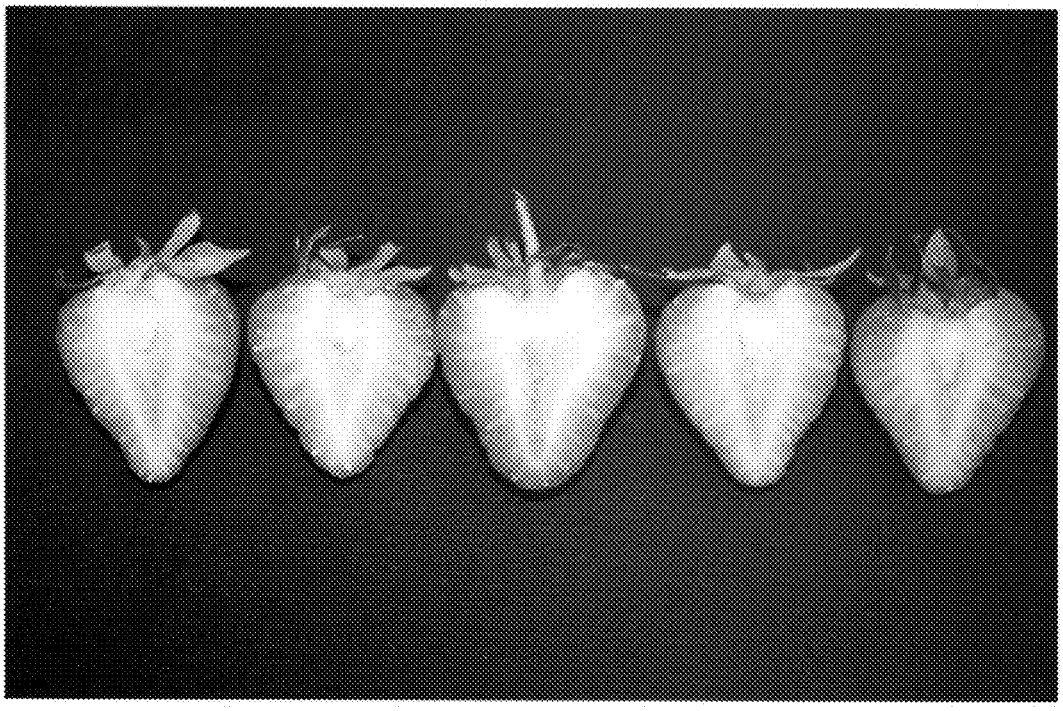
FIG. 4 shows the fruit in longitudinal cross-section.

The following detailed descriptions set forth the distinctive characteristics of 'DrisStrawFortySix'. The data which define these characteristics is based on observations taken in Kent, United Kingdom from 2010 to 2014. This description is in accordance with UPOV terminology. Color designations, color descriptions, and other phenotypical descriptions may deviate from the stated values and descriptions depending upon variation in environmental, seasonal, climatic, and cultural conditions. 'DrisStrawFortySix' has not been observed under all possible environmental conditions. The botanical description of 'DrisStrawFortySix' was taken from ten to twelve-month-old plants. Color references are primarily to The R.H.S. Colour Chart of The Royal Horticultural Society of London (R.H.S.) (2007 edition). Descriptive terminology follows the *Plant Identification Terminology, An Illustrated Glossary,* $2^{nd}$ edition by James G. Harris and Melinda Woolf Harris, unless where otherwise defined.

DETAILED BOTANICAL DESCRIPTION OF THE PLANT

Classification:
- *Species.*—*Fragaria×ananassa.*
- *Common name.*—Strawberry.
- *Denomination.*—'DrisStrawFortySix'.

Parentage:
- *Female parent.*—The proprietary variety 'DrisStrawThirtyTwo' (U.S. Plant Pat. No. 24,333).
- *Male parent.*—The proprietary variety 'KGEM 0631-001' (unpatented).

Plant:
- *Height.*—48.4 cm.
- *Diameter.*—42.5 cm.
- *Number of crowns/plant.*—6.
- *Habit.*—Globose — semi-upright.
- *Density of individual plant.*—Medium.
- *Vigor* (*health and hardiness of plant*).—Medium.

Terminal leaflets:
- *Size.*—Small. Length: 9.1 cm. Width: 8.3 cm. Length/width ratio: 1.1 (Longer than broad).
- *Number of teeth/terminal leaflet.*—19.
- *Shape of teeth.*—Obtuse — serrate to crenate.
- *Color.*—Upper surface: RHS N137B (Dark green). Lower surface: RHS 137B (Medium green).
- *Shape in cross section.*—Slightly concave.
- *Blistering.*—Weak.
- *Glossiness.*—Medium.
- *Number of leaflets.*—Three only.
- *Shape.*—Orbicular.
- *Base shape.*—Slightly oblique.
- *Apex descriptor.*—Rounded.
- *Margin.*—Crenate.
- *Margin profile.*—Revolute (margins rolled backwards).
- *Variegation.*—Absent.

Petiole:
- *Length.*—Long; 36.5 cm.
- *Diameter.*—6.2 mm.
- *Pubescence.*—Medium.
- *Pose of hairs.*—Slightly upwards.
- *Color.*—RHS 144B (Medium yellow-green).
- *Bract frequency.*—0.

Petiolule:
- *Length.*—7.14 mm.
- *Diameter.*—2.10 mm.
- *Color.*—RHS 144D (Light yellow-green).

Stipule:
- *Length.*—3.9 cm.
- *Width.*—9.51 mm.
- *Pubescence.*—Absent or very sparse.
- *Stipule anthocyanin coloration.*—Medium; RHS 63C (Medium red-purple).

Stolons:
- *Number of stolons.*—Medium.
- *Average number of daughter plants* (*per square meter*).—89.
- *Anthocyanin coloration.*—Absent or very weak; RHS 144B (Medium yellow-green).
- *Diameter at bract.*—4.29 mm.
- *Thickness.*—Thick.
- *Density of pubescence.*—Medium.

Inflorescence:
- *Position relative to foliage.*—Level.
- *Number of flowers per plant.*—Many.
- *Time of flowering* (50% *of plants at first flower*).—Late April.

*Flower size*.—Medium.

*Flower diameter*.—29.00 mm.

*Petals*.—Shape: Orbicular. Apex: Rounded. Base: Concavo-convex. Margin: Entire. Spacing: Overlapping. Length: 12.12 mm. Width: 12.25 mm. Length/width ratio: 1.0 (As long as broad). Petal number per flower: 6. Color (upper surface): RHS 155C (White).

*Calyx*.—Diameter: 23.07 mm. Diameter relative to corolla: Smaller. Inner calyx diameter relative to outer: Same size. Insertion of calyx: In a basin — inserted. Pose of calyx segments: Reflexed — upwards. Size of calyx in relation to fruit: Slightly larger. Adherence of calyx: Medium.

*Sepal*.—Shape: Ovate. Apex: Truncate. Margin: Entire. Length: 8.22 mm. Width: 4.20 mm. Sepal number: 10.

*Receptacle color*.—RHS 12C (Light yellow).

*Stamen*.—Present. Anther color: RHS 153B (Medium yellow-green).

*Pedicel*.—Attitude of hairs: Slightly upwards.

Fruiting truss:

*Length*.—Medium; 43.4 cm.

*Diameter at base of truss*.—5.80 mm.

*Number of berries per fruiting truss*.—8.

*Attitude at first picking*.—Semi-erect.

*Color at base of truss*.—RHS 144C (Medium yellow-green).

Fruit:

*Relative fruit size*.—Medium.

*Length*.—42.98 mm.

*Width*.—38.57 mm.

*Length/width ratio*.—1.1 (Longer than broad).

*Fruit hollow length*.—33.27 mm.

*Fruit hollow width*.—15.30 mm.

*Fruit hollow length/width ratio*.—2.2 (Longer than broad).

*Fruit hollow center* (*cavity*).—Medium.

*Fruit weight*.—24.0 g.

*Predominant fruit shape*.—Conical.

*Difference in shape between primary and secondary fruits*.—None or very slight.

*Evenness of fruit surface*.—Even or very slightly uneven.

*Fruit skin color*.—RHS 44A (Medium red).

*Evenness of fruit color*.—Even or very slightly uneven.

*Fruit glossiness*.—Medium.

*Achenes*.—Insertion of achenes: Below surface. Coloration (sunward side of berry): RHS 174A. Coloration (shaded side of berry): RHS 174B. Number per berry: 192. Weight (weight of achenes divided by total # seed): 0.006 g. Width of band without achenes: Narrow.

*Firmness of flesh* (*when fully ripe*).—Firm.

*Color of flesh* (*excluding core*).—RHS 40C (Light red).

*Color of core*.—RHS 37A (Light red).

*Evenness of flesh color*.—Even.

*Distribution of flesh color*.—Marginal and central.

*Sweetness*.—8.5 degree Brix. Texture when tasted: Fine.

*Type of bearing*.—Not everbearing — not remontant.

*Harvest interval*.—Late May-mid-July.

*Harvest maturity*.—Early.

*Production*.—1079 grams per plant in Class I & II UK (2012-2014).

Disease and pest resistance: Not tested.

COMPARISON WITH PARENTAL AND COMMERCIAL VARIETIES

When 'DrisStrawFortySix' is compared to the female parent 'DrisStrawThirtyTwo' (U.S. Plant Pat. No. 24,333), 'DrisStrawFortySix' is higher yielding and has a lighter red color and better flavor than 'DrisStrawThirtyTwo'.

When 'DrisStrawFortySix' is compared to the male parent 'KGEM 0631-001' (unpatented), 'DrisStrawFortySix' is higher yielding and has slightly larger fruit than 'KGEM 0631-001'.

'DrisStrawFortySix' differs from the commercial variety 'Sonata' (U.S. Plant Pat. No. 18,000), in that 'DrisStrawFortySix' has fruit with a medium-sized hollow center and achenes that are inserted below the fruit surface, whereas 'Sonata' has an absent or weakly expressed hollow center and achenes that are inserted level with the fruit surface. Additionally, 'DrisStrawFortySix' has a globose—semi-upright habit, whereas 'Sonata' has an upright and open plant habit.

'DrisStrawFortySix' differs from the commercial variety 'Elsanta' (unpatented), in that 'DrisStrawFortySix' has medium-sized fruit with medium glossiness and a light red colored core, whereas 'Elsanta' has large, glossy fruit with a white colored core.

We claim:

1. A new and distinct variety of strawberry plant named 'DrisStrawFortySix', substantially as illustrated and described herein.

* * * * *